United States Patent [19]

Laerum

[11] Patent Number: 4,987,122
[45] Date of Patent: Jan. 22, 1991

[54] PEPTIDE COMPOUNDS AND MEDICAL METHOD OF USE THEREOF

[75] Inventor: Ole D. Laerum, Bergen, Norway

[73] Assignee: Nycomed AS, Oslo, Norway

[21] Appl. No.: 206,341

[22] PCT Filed: Nov. 5, 1987

[86] PCT No.: PCT/GB87/00784
  § 371 Date: Jun. 17, 1987
  § 102(e) Date: Jun. 17, 1987

[87] PCT Pub. No.: WO88/03535
  PCT Pub. Date: May 19, 1988

[30] Foreign Application Priority Data

Nov. 6, 1986 [GB] United Kingdom ............... 8626539

[51] Int. Cl.$^5$ .......................... C07K 5/10; C07K 7/06; A61K 37/02

[52] U.S. Cl. ........................................ 514/15; 514/16; 514/17; 514/18; 530/328; 530/329; 530/330

[58] Field of Search ...................... 514/15, 16, 17, 18; 530/328, 329, 330

[56] References Cited

PUBLICATIONS

Paukovits et al., Chem. Absts., vol. 98, No. 9, Abst. No. 67383u, 1983.
Foa et al., Chem. Absts., vol. 99, No. 1, Abst. No. 1022q, 1983.

*Primary Examiner*—David B. Springer
*Attorney, Agent, or Firm*—Bacon & Thomas

[57] ABSTRACT

Novel peptides consisting of dimeric peptide chains linked by a disulphide bridge. The dimers have a stimulatory effect on haemopoiesis, by contrast with the inhibitory effect of the monomer analogues.

6 Claims, No Drawings

PEPTIDE COMPOUNDS AND MEDICAL METHOD OF USE THEREOF

The present invention relates to novel peptides having a stimulatory effect on haemopoiesis and to a process for their preparation.

The bone marrow cells derive from pluripotent stem cells which mature to form a complex population of morphologically distinct cells, namely megakaryocytes, erythrocytes, granulocytes and lymphocytes. Only about 10% of the stem cells are in cell division at any time. In an initial phase of maturation each of the proliferating stem cells becomes "committed" to a particular morphologically distinct form eventually leading to one of the above four mature cell types. As the cells proliferate they gradually lose the power of further proliferation and the mature cells, for example, erythrocytes or granulocytes, can no longer divide. Consequently, since the mature cells are continually dying, it is essential that the proliferative ability of the less mature cells, and in particular the stem cells committed for myelopoesis, is maintained.

We have now found a group of novel peptides which are capable of stimulating the proliferation of myelopoietic stem cells.

According to the present invention, therefore, we provide compounds of the formula (I):

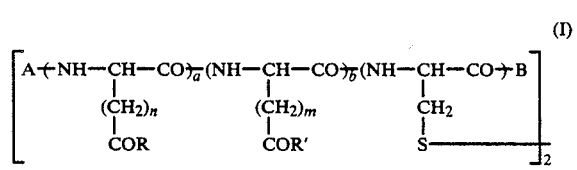

wherein all amino acid units are in the L-configuration, A represents

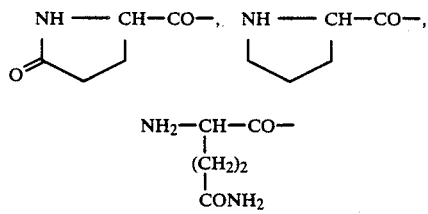

or a hydrogen atom; B represents

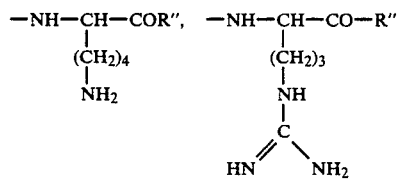

or a hydroxy group; n and m independently represent the integers 1 or 2; a and b independently represent the integers 0 or 1; R, R' and R" independently represent a hydroxy group or an amino group; and the physiologically acceptable salts thereof with the proviso that when A and B represent a hydrogen atom and a hydroxy group respectively, b may not represent the integer 0.

The compounds of formula (I) are thus symmetrical dimers.

When A represents a glutamine residue or a proline residue it is preferred that $a=b=1$, $n=2$, $m=1$, R and R' represent hydroxy groups and B represents a lysine residue.

When B represents an arginine residue it is preferred that A represents a pyroglutamate residue, $a=b=1$, $n=2$, $m=1$ and R and R' represent hydroxy groups.

A preferred group of compounds are those in which $b=1$, $m=1$ and R, R' and R" represent hydroxy groups. Particularly preferred compounds according to the invention are as follows (using the conventional biochemical notation for the amino acids and reading from the N-terminus):

(Cys - Lys)$_2$ (Asp - Cys - Lys)$_2$ (Glu - Asp - Cys - Lys)$_2$ (pGlu - Glu - Asp - Cys)$_2$ (pGlu - Asp - Cys - Lys)$_2$ (pGlu - Asp - Asp - Cys - Lys)$_2$ (pGlu - Glu - Asp - Cys - Arg)$_2$ (Gln - Glu - Asp - Cys - Lys)$_2$ (Pro - Glu - Asp - Cys - Lys)$_2$

A further particularly preferred compound is (pGlu-Glu-Asp-Cys-Lys)$_2$ i.e. the compound in which $a=b=1$, $m=1$, $n=2$, R and R' represent hydroxy groups, A represents a pyroglutamate residue and B represents a lysine redidue.

Physiologically acceptable salts of the peptides of the invention include acid addition salts such as the hydrochloride, hydrobromide, sulphate, etc. as well as salts with bases such as alkali metal salts, e.g. sodium or potassium salts, alkaline earth metal salts, e.g. the calcium salt or amine salts.

Some of the compounds of formula (I) are dimers of compounds described and claimed in our European Patent Application No. 83307210.1. This latter application relates to a small group of haemoregulatory peptides having an inhibitory effect on granulopoiesis.

Due to the minute amounts of the natural granulopoiesis factor available, the structure of the natural substance has never been determined. It has never been obtained in crystalline or completely pure form and it is not known whether this could be achieved using material from natural sources only. It has been postulated as having the structure pyroGlu-Asp-Asp-Cys-LysOH but, as reported in our above European patent application, the synthetic compound having this structure proved to be inactive. It has been observed that when the natural granulopoiesis inhibition factor is subjected to oxidising conditions, a compound having stimulatory action was produced. However, this product has also never been isolated or identified. In contrast, the peptides of the invention can be obtained in pure form suitable for pharmaceutical use and in relatively large quantities.

It has also been reported (Exp. Hematol. 12 7 (1981)) that when one of the peptides in our above European patent application, namely pyroGlu-Glu-Asp-Cys-LysOH, is subjected to freezing and thawing it exhibits stimulatory activity which can be reversed by treatment with mercaptoethanol. However the stimulatory product was never obtained in pure form and its structure was never determined.

The new compounds in chemically pure form have been tested for in vitro and in vivo haemoregulatory effects. In vitro studies of both human and mouse myelopoietic stem cells have shown increases in agar colony formation of up to 1500%. The stimulatory effect occurs in the concentration range $10^{-13}$ to $10^{-5}$ M. In in vivo studies in mice, we have found that a single injection can increase the number of myelopoietic stem cells by 50% within 48 hours and, by continuous infusion, the number of stem cells was doubled within 13 days.

The invention is of particular application in stimulating myelopoiesis in patients suffering from reduced myelopoietic activity, including bone marrow damage, agranulocytosis and aplastic anaemia. This includes treatment of patients having depressed bone marrow function due to immunosuppressive treatment to suppress tissue reactions, e.g. in bone marrow transplant surgery.

The compounds may also be used to promote more rapid regeneration of bone marrow after cytostatic chemotherapy and radiation therapy for neoplastic and viral diseases.

In addition, the new compounds may be of particular value where patients have serious infections due to lack of immune response following bone marrow failure.

Another clinical application will be in combination with the corresponding monomers or related myelopoiesis inhibitors as disclosed in our above European Patent Specification to induce alternating peaks of high and low activity in the bone marrow cells, thus augmenting the natural circadian rhythm of haemopoiesis. In this way, cytostatic therapy can be given at periods of low bone marrow activity, thus reducing the risk of bone marrow damage, while regeneration will be promoted by the succeeding peak of activity.

It should be noted that there is no stimulatory effect on the cells of other tissues and in particular on tumour cells related to non-myelopoietic tissues. The new compounds thus stimulate the myelopoietic system selectively, The peptides are without significant toxicity. Furthermore, all the haematological effects observed are reversible and no macroscopic changes were observed in the other organs of the animals injected with the peptides.

In general, in order to exert a stimulatory effect, the peptides of the invention may be administered to human patients by injection in the dose range 0.1–10 mg, for example 1–5 mg, per 70 kg body weight per day. If administered by infusion or similar techniques, the dose may be in the range 30–300 mg per 70 kg body weight, for example about 100 mg, over six days. In principle it is desirable to produce a concentration of the peptide of about $10^{-13}M$ to $10^{-5}M$ in the extracellular fluid of the patient.

According to a still further feature of the present invention there is provided pharmaceutical compositions comprising as active ingredient one or more compound of formula (I) as hereinbefore defined or physiologically compatible salts thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

According to a still further feature of the present invention there is provided a method of stimulation of myelopoiesis which comprises administering an effective amount of a pharmaceutical composition as hereinbefore defined to a subject.

A further major use of the new peptides, however, is in the production of material for immunological assay techniques. The peptide may then be covalently attached to a suitable high molecular carrier such as albumin, polylysine or polyproline in order to be injected into antibody-producing animals (e.g. rabbits, guinea pigs or goats). In vitro immunisation techniques may also be used. High specificity antisera are obtained by use of well known absorption techniques, using the high molecular carrier. By introducing radioactivity ($^3H$, $^{14}C$, $^{35}S$) into the peptide molecule, a radioimmuno assay can readily be designed and used for determining the peptide in the different biological fluids such as serum (plasma), urine and cerebrospinal fluid.

The peptides of the invention may be synthesised in any convenient way. In general, the reactive side chain groups present (amino, thiol and/or carboxyl) will be protected during the coupling reactions of the overall synthesis and the final stage will thus be the deprotection of a protected derivative of formula (I). Normally, all —COOH groups, all —NH$_2$ groups and the —NH group of the pyroglutamyl or proline residue will be protected; such protected forms of the peptides form a further feature of the invention and have the general formula (II)

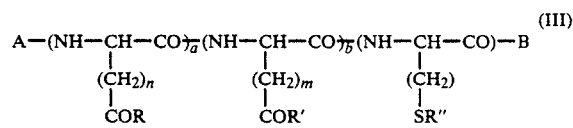

wherein
A represents

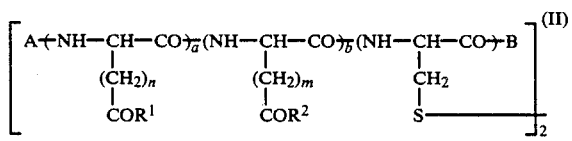

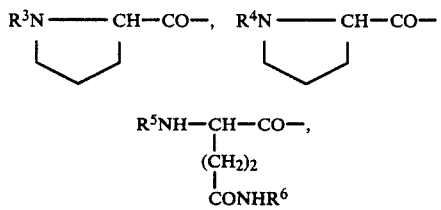

a hydrogen atom or an amine protecting group;
B represents

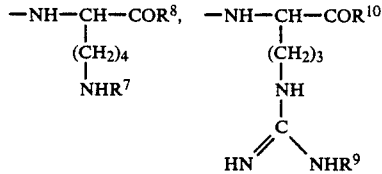

a hydroxy group or a carboxyl blocking group;
n and m independently represent the integers 1 or 2;
a and b independently represent the integers 0 or 1;
$R^1$, $R^2$, $R^8$ and $R^{10}$ are amino, hydroxy, protected amino or carboxyl protecting groups;
$R^3$, $R^4$, $R^5$, $R^6$, $R^7$ and $R^9$ are hydrogen atoms or amine protecting groups;
with the proviso that when A represents a hydrogen atom or an amine protecting group and B represents a hydroxy group or a carboxyl blocking group then b may not represent the integer zero.

In general, the protected derivatives of formula (II) can be prepared by way of the techniques appropriate for peptide synthesis.

One possible synthetic route utilises cystine and couples this to the remaining amino acid residues so that the two identical chains of the dimer are assembled and linked via the disulphide bond already present in cystine. An alternative strategy is to synthesise the corresponding monomeric compound in S-protected form, using S-protected cysteine, to remove the S-protecting group and to effect dimerisation. It is possible to use S-protecting groups which can be removed by oxidising agents creating a disulphide bond directly in the deprotecting step; thus for example trityl groups can be selectively removed by iodine, preferably in a suitable solvent such as dimethylformamide; such dimerisation may be effeted on the C— and N protected monomer, followed by removal of the C— and N— protecting groups, or may be effected as the final synthesis step using a monomer of the formula (III)

$$A-(NH-CH-CO)_{\overline{a}}(NH-CH-CO)_{\overline{b}}(NH-CH-CO)-B \quad (III)$$
$$\begin{array}{ccc} (CH_2)_n & (CH_2)_m & (CH_2) \\ COR & COR' & SR'' \end{array}$$

wherein A, B, n, m, a, b, R and R' are as defined above and R" is a hydrogen atom or a thiol protecting group removable under oxidising conditions.

In building up the peptide chains, one can in principle, start either at the C-terminal or the N-terminal although only the C-terminal starting procedure is in common use.

Thus, one can start at the C-terminal by reaction of a suitably protected derivative of, for example lysine with a suitably protected derivative of cysteine or cystine. The lysine derivative will have a free α-amino group while the other reactant will have either a free or activated carboxyl group and a protected amino group. After coupling, the intermediate may be purified, for example by chromatography, and then selectively N-deprotected to permit addition of a further amino acid residue. This procedure is continued until the required amino acid sequence is completed.

Carboxylic acid activating substituents which may, for example, be employed include symmetrical or mixed anhydrides, or activated esters such as for example the p-nitrophenyl ester, 2,4,5-trichlorophenyl ester, N-hydroxybenzotriazole ester (OBt), or N-hydroxysuccinimidyl ester (OSu).

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start at the C-terminal, for example by coupling N-protected lysine to the support.

A number of suitable solid phase techniques are described by Eric Atherton, Christopher J. Logan, and Robert C. Sheppard J. Chem. Soc. Perkin I, 538–46 (1981); James P. Tam, Foe S. Tjoeng, and R. B. Merrifield J. Am. Chem. Soc. 102 6117-27 (1980); James P. Tam, Richard D. Dimarchi and R. B. Merrifield Int. J. Peptide Protein Res 16 412-25 (1980); Manfred Mutter and Dieter Bellof, Helvetica Chimica Acta 67 2009-16 (1984).

A wide choice of protecting groups for amino-acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag, Stuttgart 1974; Amino Acids, Peptides and Proteins, Vol. 4–8, The Chemical Society, London 1972, 1974, 1975 and 1976; Peptides, Synthesis-physical data 1–6, Wolfgang Voelter, Eric Schmidt-Siegman, Georg Thieme Verlage Stuttgart, N.Y., 1983; The Peptides, Analysis, synthesis, biology 1–7, Ed: Erhard Gross, Johannes Meienhofer, Academic Press, N.Y., San Francisco, London; Solid phase peptide synthesis 2nd ed., John M. Stewart, Janis D. Young, Pierce Chemical Company.

Thus, for example amine protecting groups which may be employed include protecting groups such as carbobenzoxy (hereinafter also designated Z) t-butoxycarbonyl (hereinafter also designated Boc), 4-methoxy-2,3,6-trimethylbenzene sulphonyl (Mtr) and 9-fluorenylmethoxycarbonyl (hereinafter also designated Fmoc). It will be appreciated that when the peptide is built up from the C-terminal end, an amine-protecting group will be present on the E-amino group of each new residue added and will need to be removed selectively prior to the next coupling step. One particularly useful group for such temporary amine protection is the Fmoc group which can be removed selectively by treatment with piperidine in an organic solvent.

Carboxyl protecting groups which may, for example be employed include readily cleaved ester groups such as benzyl (Bzl), p-nitrobenzyl (ONb), pentachlorophenyl (OPClP), pentafluorophenyl (OPFP) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary $\alpha$-amino protecting group prior to the next coupling step.

Amine protecting groups such as Boc and carboxyl protecting groups such as tBu may be removed simultaneously by acid treatment, for example with trifluoro acetic acid. Thiol protecting groups such as Trt may be removed selectively using an oxidation agent such as iodine.

The following Examples are given by way of illustration only.

Solvents were redistilled from commercial material and stored in the following way: Dimethylformamide (DMF) over molecular sieve 4A, dichloromethane (DCM) over $CaCl_2$, triethylamine (TEA) over Na/Pb alloy (Baker) and trifluoroacetic acid (TFA) over molecular sieve 4A. TLC systems were as follows:

$S_1$: Silica/$CHCl_3$: MeOH (98:2)

$S_2$: Silica/$CHCl_3$: MeOH (95:5)
$S_3$: Silica RP 8/0.1% TFA in 5% EtOH (aq).

The purified end products were analyzed by reversed phase high performance liquid chromatography (HPLC). The HPLC-system consisted of a HP 1090M chromatograph with an in-built autosampler and a HP 1040 diode array (Hewlett-Packard, Waldbronn, FRG), and a supelcosil LC-18 column (250×4.6 mm, 5u particles). Samples were dissolved in 0.1% (v/v) TFA (aq) and eluted with a linear gradient from 0 to 30% acetonitrile in 0.1% TFA (aq.). The flow rate was 2ml/min. The eluent was monitored at 214 nm with a bandwidth of 4nm. The solvent chromatogram was electronically subtracted, and the results were presented in terms of area percent.

Amino Acid Analysis

The cystine containing peptides were oxidized by performic acid to convert the acid labile cystine residue to the acid stable cysteic acid, before acid hydrolysis in 6 M HCl at 110° C. for 16 hours. The dry hydrolysates were then derivatised by the use of phenyl isothiocyanate and analysed as described by Heinrikson (Anal. Bioch. 136, 65–74, 1984).

EXAMPLE 1

(pGlu-Glu-Asp-Cys-Lys)$_2$
(Fmoc-Cys-Lys(N$\epsilon$-Boc)-OtBu)$_2$ (1)

2 g (2.275 mM) (Fmoc-Cys-OSu)$_2$, 2.18 g (5.0 mM) Lys(N$\epsilon$-Boc)-OtBu.HCl and 0.58 g (5 mM) N-ethyl-morpholine were dissolved in 7.5 ml DMF and stirred at room temperature for three hours. The reaction mixture was evaporated to dryness under reduced pressure. The residue was dissolved in 50 ml $CHCl_3$ and washed with 3×12 ml 0.1 N HCl and 3×12 ml 1 M NaCl. The organic layer was filtered through a phase separation filterpaper (Whatman) and evaporated to dryness under reduced pressure.

The crude product (3.32 g) was recrystallized from 5 ml warm MeOH (15 hours), filtered, washed with MeOH and ether and air dried. Yield: 1.75 g (61%). The white solid showed one major spot (UV$_{254}$+, $Cl_2$/dicarboxidin+, ninhydrin÷) on TLC ($S_1$: Rf=0.667, $S_2$: Rf=0.829).

(Cys-Lys(N$\epsilon$-Boc)-OtBu)$_2$ (2)

1.5 g (1.19 mM) of compound (1) was dissolved in 10 ml 20% piperidine in DMF and stirred at room temperature for 30 minutes. TLC ($S_2$) showed that all starting material was consumed and only one new product (UV$_{254}$÷, $Cl_2$/dicarboxidin+, ninhydrin+) was formed. The solvent was evaporated under reduced pressure. The residue was dissolved in 20 ml ether and washed with 2×3 ml 0.1N HCl and 3 ml 1M $NaHCO_3$. The organic layer was filtered through a phase separation filterpaper and evaporated to dryness.

Yield: 1.2 g. TLC showed only one ninhydrin positive component ($S_2$: Rf=0.216).

(Fmoc-Asp($\beta$-OtBu)-Cys-Lys(N$\epsilon$-Boc)-OtBu)$_2$ (3)

Approximately 1.19 mM of compound (2) and 1.32 g (2.6 mM) Fmoc-Asp($\beta$-OtBu)-OSu were dissolved in 6 ml $CH_2Cl_2$ and stirred at room temperature for two hours. TLC ($S_1$) showed that all ninhydrin positive material was consumed and that one new major $UV_{254}$ positive product had been formed. The residue after evaporation was dissolved in 30 ml EtOAc, washed with 4×10 ml 1M NaCl, filtered and evaporated as described for (1). The crude product was dissolved in ether (2.5 ml) and precipitated as a semicrystalline solid by adding 4 ml n-hexane (refrigerator 16 hours). Solvent was decanted, the product washed with 5 ml n-hexane and dried under reduced pressure. Yield: 1.272 g (67%). TLC showed one major spot ($UV_{254}+$, $Cl_2$/dicarboxidine+, ninhydrin÷, $S_1$: $Rf=0.333$, $S_2$: $Rf=0.658$).

(Asp($\beta$8-OtBu)-Cys-Lys(N$\epsilon$-Boc)-OtBu)$_2$ (4)

1.0 g (0.62 mM) of compound (3) was dissolved in 5 ml 20% piperidine in $CH_2Cl_2$ and treated as described for 2. Yield: 0.469 g (65%) TLC showed only one ninhydrin positive spot ($S_2$: $Rf=0.22$).

(Fmoc-Glu($\gamma$-OtBu)-Asp($\beta$-OtBu)-Cys-Lvs(N$\epsilon$-Boc)-OtBu)$_2$ (5)

0.469 g (0.407 mM) of compound (4) and 0.47 g (0.90 mM) Fmoc-Glu($\gamma$-OtBu)-OSu were dissolved in 5 ml $CH_2Cl_2$ and stirred at room temperature for 15 hours. Work up procedure was as for (3).

Yield: 0.62 g (77%). TLC showed one major spot ($UV_{254}+$, $Cl_2$/dicarboxidin +, ninhydrin÷$S_1$: $Rf=0.312$, $S_2$: $Rf=0.536$).

(Glu($\gamma$-OtBu)-Asp($\beta$-OtBu)-Cys-Lys(N$\epsilon$-Boc)-OtBu)$_2$ (6)

0.50 g (0.25 mM) of compound (5) was dissolved in 2.5 ml 20% piperidine in $CH_2Cl_2$ and treated as described for (2).

TLC showed only one ninhydrin positive spot ($S_2$: $Rf=0.154$).

(pGlu-Glu($\gamma$-OtBu)-Asp($\beta$-OtBu)-Cys-Lys(N$\epsilon$-Boc)-OtBu)$_2$ (7)

Approximately 0.25 mM of compound (6) and 0.206 g (0.546 mM) pGlu-OPClP were dissolved in 2.5 ml DMF and stirred at room temperature for 15 hours. Work up procedure was as for (3).

Yield: 0.259 g (59%). TLC showed only one spot $UV_{254}\div$, ninhydrin÷ and $Cl_2$/dicarboxidine+($S_2$: $Rf=0.117$) and only traces of impurities.

(pGlu-Glu-Aso-Cys-Lys)$_2$ (8)

0.110 g (0.063 mM) of compound (7) was dissolved in 5 ml 80% TFA ($CH_2Cl_2$) and stirred at room temperature for 30 minutes. The solvent was evaporated and the residue was dissolved in 4 ml $H_2O+2$ ml $CHCl_3$. The water phase was washed with 2×3 ml $CHCl_3$ and evaporated to dryness under reduced pressure. The crude product (0.050 g) was purified on a Lobar (A) RP 8 column (Merck) eluted with 0.1% TFA in 7.5 EtOH (aq.) After lyophilization of the product it was rechromatographed on the same column eluted by 0.1% TFA in 5% EtOH (aq.) The product was lyophilized.

Yield: 0.016 g. The ninhydrin+, $Cl_2$/dicarboxidine+ and $UV_{254}\div$ product was homogeneous by TLC, ($S_3$: $Rf=0.436$), and only traces of impurities were detected by HPLC.

Amino acid analysis: Asp (1.02), Glu (1.91), Cys(1.08), Lys (0.93).

EXAMPLE 2

(Cys-Lys)$_2$, (9)

Compound (2) from Example 1 was dissolved in TFA and stirred at ambient temperature for 40 minutes. The solvent was evaporated under reduced pressure (30° C.) and the water soluble part of the residue was chromatographed on a lobar(B)RP8 column (Merck) using 0.1% TFA (aq.) in 5% EtOH (aq.) as mobile phase. The column was monitored at $UV_{220}$. Fractions containing pure product (TLC) were pooled and lyophilized. The product was homogenous by TLC ($S_3$: $Rf=0.57$) and showed a positive reaction with ninhydrin and no $UV_{254}$ absorption. HPLC-analysis: 93.5% pure by area. Amino acid analysis: Cys (1.01), Lys (0.99).

EXAMPLE 3

(Asp-Cys-Lys)$_2$, (10)

Compound (4) treated as described in example 2 (2% EtOH in mobile phase) gave compound (10). The product was homogenous by TLC ($S_3$: $Rf=0.64$) and showed a positive reaction with ninhydrin and no $UV_{254}$ absorption. HPLC-analysis: 97.9% pure by area. Amino acid analysis : Asp (0.99), Cys (1.03), Lys (0.98).

EXAMPLE 4

(Glu-Asp-Cys-Lys)$_2$, (11)

Compound (6) treated as described in example 2 gave compound (11). The product was homogenous by TLC ($S_3$: $Rf=0.83$) and showed a positive reaction with ninhydrin and no $UV_{254}$ absorption. HPLC-analysis: 100% pure by area. Amino acid analysis : Asp (1.08), Cys (0.97), Glu (0.98), Lys (0.98).

EXAMPLE 5

(pGlu-Glu-Asp-Cys)$_2$, (12)

Compound (12) was synthesizeed as monomer by the continuous flow solid phase peptide synthesis method using a Biolynx 4170 automated peptide synthesiser (LKB) and DMF as solvent.

Reagents : FMOC-Cys(Trt)-SASRIN-RESIN (Bachem); Fmoc-Asp($\beta$-OtBu)-OPFP; FMOC-Glu($\gamma$-OtBu)-OPFP; pGlu-OPCLP; HOBT as catalyst. FMOC was removed after each coupling step by 20% piperidine in DMF. The disulphide bridge and thereby the dimer was established by treating the fully protected peptide on the solid support with 0.1M iodine (2–3eqv.) in DMF for 15 minutes. After washing with DMF the peptide was detached from the solid support and remaining protecting groups removed in one step by treatment with 50% TFA in $CH_3Cl$ for 40 minutes. The resin was filtered off and the filtrate was evaporated to dryness under reduced pressure (30° C.). The residue was dissolved in 0.1% TFA (aq.) and chromatographed on a lobar(B)RP8 column using 0.1% TFA (aq.) in 4% propan-2-ol (aq.) as mobile phase. The column was monitored at $UV_{220}$. Fractions containing pure product (HPLC) were pooled and lyophilized. The product showed no reaction with ninhydrin and no $UV_{254}$ absorption. HPLC-analysis: 96.9% pure by area. Amino acid analysis : Asp (1.15), Cys (0.99), Glu(1.85).

EXAMPLE 6

(pGlu-Glu-Cys-Lys)$_2$, (13)

Compound (13) was synthesized and purified as described in example 5 using the corresponding amino acid derivatives. Reagents not described earlier : FMOC-Lys(Nε-BOC)-SASRIN-RESIN; FMOC-Cys(S-Trt)-OPFP. The product was homogeneous by TLC (S3: Rf=0.49) and showed a positive reaction with ninhydrin and no UV254 absorption.

HPLC-analysis : 100% pure by area. Amino acid analysis: Cys (1.01), Glu(1.98), Lys(1.01).

EXAMPLE 7

(pGlu-Asp-Cys-Lys)2, (14)

Compound (14) was synthesized and purified as described in example 5 using the corresponding amino acid derivatives. The product was homogeneous by TLC (S3: Rf=0.55) and showed a positive reaction with ninhydrin and no UV254 absorption.

HPLC-analysis : 97.5% pure by area. Amino acid analysis : Asp (1.04), Cys(0.96), Glu (0.97), Lys (1.02).

EXAMPLE 8

(pGlu-Asp-Glu-Cys-Lys)2, (15)

Compound (15) was synthesized and purified as described in example 5 using the corresponding amino acid derivatives. The product was homogenous by TLC (S3: Rf=0.42) and showed a positive reaction with ninhydrin and no UV254 absorption.

HLPC-analysis : 99.3% pure by area. Amino acid analysis : Asp (1.03), Cys (0.96), Glu(2.09), Lys (0.94).

EXAMPLE 9

(pGlu-Asp-Asp-Cys-Lys)b 2, (16)

Compound (16) was synthesized and purified as described in example 5 using the corresponding amino acid derivatives. The product was homogenous by TLC (S3: Rf=0.38) and showed a positive reaction with ninhydrin and no absorption.

HPLC-analysis: 100% pure by area. Amino acid analysis : Asp (2.06), Cys (0.98), Glu (0.98), Lys (0.98).

EXAMPLE 10

(pGlu-Glu-Glu-Cys-Lys)2, (17)

Compound (17) was synthesized and purified as described in example 5 using the corresponding amino acid derivatives. The product was homogenous by TLC (S3: Rf=0.39) and showed a positive reaction with ninhydrin and no UV254 absorption.

HPLC-analysis: 99.9% pure by area. Amino acid analysis : Cys (0.95), Glu (2.90), Lys (1.15).

EXAMPLE 11

(pGlu-Glu-Asn-Cys-Lys)2, (18)

Compound (18) was synthesized and purified as described in example 5 using the corresponding amino acid derivatives. Reagents not described earlier: FMOC-Asn-OPFP. The product was homogenous by TLC (S3: Rf=0.42) and showed a positive reaction with ninhydrin and no UV254 absorption.

HPLC-analysis : 98.2% pure by area. Amino acid analysis : Asx (1.1), Cys (1.03), Glu (1.9), Lys (0.96).

EXAMPLE 12

(pGlu-Gln-Asp-Cys-Lys)2, (19)

Compound (19) was synthesized and purified as described in example 5 using the corresponding amino acid derivatives. Reagents not described earlier: FMOC-Gln-OPFP. The product was homogenous by TLC (S3: Rf=0.45) and showed a positive reaction with ninhydrin and no UV254 absorption.

HPLC-analysis: 98.3% pure by area. Amino acid analysis: Asp (1.09), Cys (1.06), Glx (1.89), Lys (0.96).

EXAMPLE 13

(pGlu-Glu-Asp-Cys-Arg)2, (20)

Compound (20) was synthesized and purified (5% propan-2-ol in mobile phase) as described in example 5 using the relevant amino acid derivatives. Final deprotection was performed in 10% thioanisole in TFA.

Reagents not described earlier: FMOC-Arg(Mtr)-SASRIN-RESIN.

The product showed no reaction with ninhydrin and no UV254 absorption.

HPLC-analysis: 99.4% pure by area. Amino acid analysis : Arg (0.92) Asp (1.12), Cys (1.00), Glu (1.96).

EXAMPLE 14

(Gln-Glu-Asp-Cys-Lys)2, (21)

Compound (21) was synthesized and purified as described in example 5 using the relevant amino acid derivatives. The product was homogenous by TLC (S3: Rf=0.57) and showed a positive reaction with ninhydrin and no UV254 absorption.

HPLC-analysis: 94.7% pure by area. Amino acid analysis : Asp (1.00), Cys (1.01), Glx (2.02), Lys (0.96).

EXAMPLE 15

(Pro-Glu-Asp-Cys-Lys)2, (22)

Compound (22) was synthesized and purified as described in example 5 using the relevant amino acid derivatives. The product was homogeneous by TLC (S3: Rf=0.57) and showed a positive reaction with ninhydrin and no UV254 absorption.

HPLC-analysis: 98.2% pure by area. Amino acid analysis : Asp (1.06) Cys (1.01), Glu (0.99), Lys (0.99), Pro (0.96).

I claim:

1. Compounds of the formula (I):

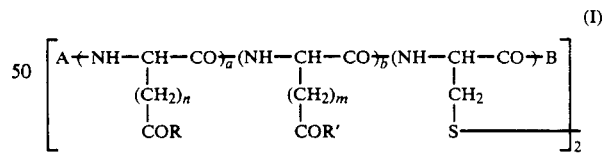

wherein all amino acid units are in the L-configuration, A represents

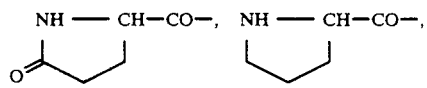

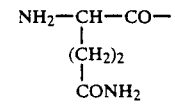

or a hydrogen atom; B represents

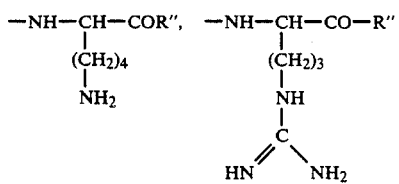

or a hydroxy group; n and m independently represent the integers 1 or 2; a and b independently represent the integers 1 or 1; R, R' and R'' independently represent a hydroxy group or an amino group; and the physiologically acceptable salts thereof with the proviso that when A and B represent a hydrogen atom and a hydroxy group respectively, b may not represent the integer 0.

2. Compounds as claimed in claim 1 wherein b represents the integer 1, m represents the integer 1 and R, R' and R'' represent hydroxy groups.

3. Compounds as claimed in claim 2 being (Cys - Lys)$_2$ (Asp - Cys - Lys)$_2$ (Glu - Asp - Cys - Lys)$_2$ (pGlu - Glu - Asp - Cys)$_2$ (pGlu - Asp - Cys - Lys)$_2$ (pGlu - Asp - Asp - Cys - Lys)$_2$ (pGlu - Glu - Asp - Cys - Arg)$_2$ (Gln - Glu - Asp - Cys - Lys)$_2$ (Pro - Glu - Asp - Cys - Lys)$_2$ 4. The compound (pGlu-Glu-Asp-Cys-Lys)$_2$ as claimed in claim 2.

5. Pharmaceutical compositions comprising as active ingredient one or more compounds of formula (I) as claimed in claim 1, or a physiologically compatible salt thereof, in association with a pharmaceutical carrier or excipient.

6. A method of stimulating the myelopoietic system of a human or animal subject in which an effective dose of a compound as claimed in claim 1 is administered to said subject.

* * * * *